US00PP14111P39

(12) United States Plant Patent
Noodelijk

(10) Patent No.: US PP14,111 P3
(45) Date of Patent: Aug. 26, 2003

(54) CHRYSANTHEMUM NAMED WHITE REAGAN MUNDO

(75) Inventor: Robert Noodelijk, Woubrugge (NL)

(73) Assignee: Chrysanthemum Breeders Association N.V. (NL)

( * ) Notice: Subject to any disclaimer, the term of this patent is extended or adjusted under 35 U.S.C. 154(b) by 356 days.

(21) Appl. No.: 09/773,608

(22) Filed: Feb. 2, 2001

(65) Prior Publication Data

US 2001/0013136 P1 Aug. 9, 2001

(51) Int. Cl.[7] ..... A01H 5/00
(52) U.S. Cl. ..... Plt./294

(58) Field of Search ..... Plt./294

(56) References Cited

PUBLICATIONS

UPOV–Rom, Retrieval Software GTI Jouve, Plant Variety Database, hits on 'White Reagan Mundo'.*

* cited by examiner

*Primary Examiner*—Bruce R. Campell
*Assistant Examiner*—Anne Marie Grünberg
(74) *Attorney, Agent, or Firm*—Parkhurst & Wendel, L.L.P.

(57) ABSTRACT

A Chrysanthemum plant named 'White Reagan Mundo' characterized by its medium sized blooms with white ray-florets and yellow-green disc florets.

1 Drawing Sheet

RELATED CULTIVARS

'White Reagan Mundo' is related to 'Pearl Reagan Mundo' (unpatented) and 'Reagan' (U.S. Plant Pat. No. 8,642). 'White Reagan Mundo' is a color mutant of 'Pearl Reagan Mundo'.

BACKGROUND OF THE INVENTION

'White Reagan Mundo' is a product of a breeding and selection program that had the objective of finding color mutants of 'Pearl Reagan Mundo'. The new plant of the present invention comprises a new and distinct cultivar of chrysanthemum plant that is a natural occuring sport of a parent chrysanthemum named 'Pearl Reagan Mundo' (unpatented). A comparison with parent chrysanthemum 'Pearl Reagan Mundo' is also made in this application. The new cultivar was discovered as a whole plant mutation in September, 1996 by Rob Noodelijk in a controlled environment (greenhouse) in Rijsenhout, Holland. The first act of asexual reproduction of 'White Reagan Mundo' was accomplished when vegetative cuttings were taken from the initial selection in November, 1996 in Rijsenhout, Holland.

SUMMARY OF THE INVENTION

The present invention is a new and distinct variety of chrysanthemum bearing medium sized blooms with white ray-florets and yellow-green disc florets.

BRIEF DESCRIPTION OF THE DRAWINGS

The present invention of a new and distinct variety of chrysanthemum is shown in the accompanying drawings, the color being as nearly true as possible with color photographs of this type.

DESCRIPTION OF THE INVENTION

Figure 1:
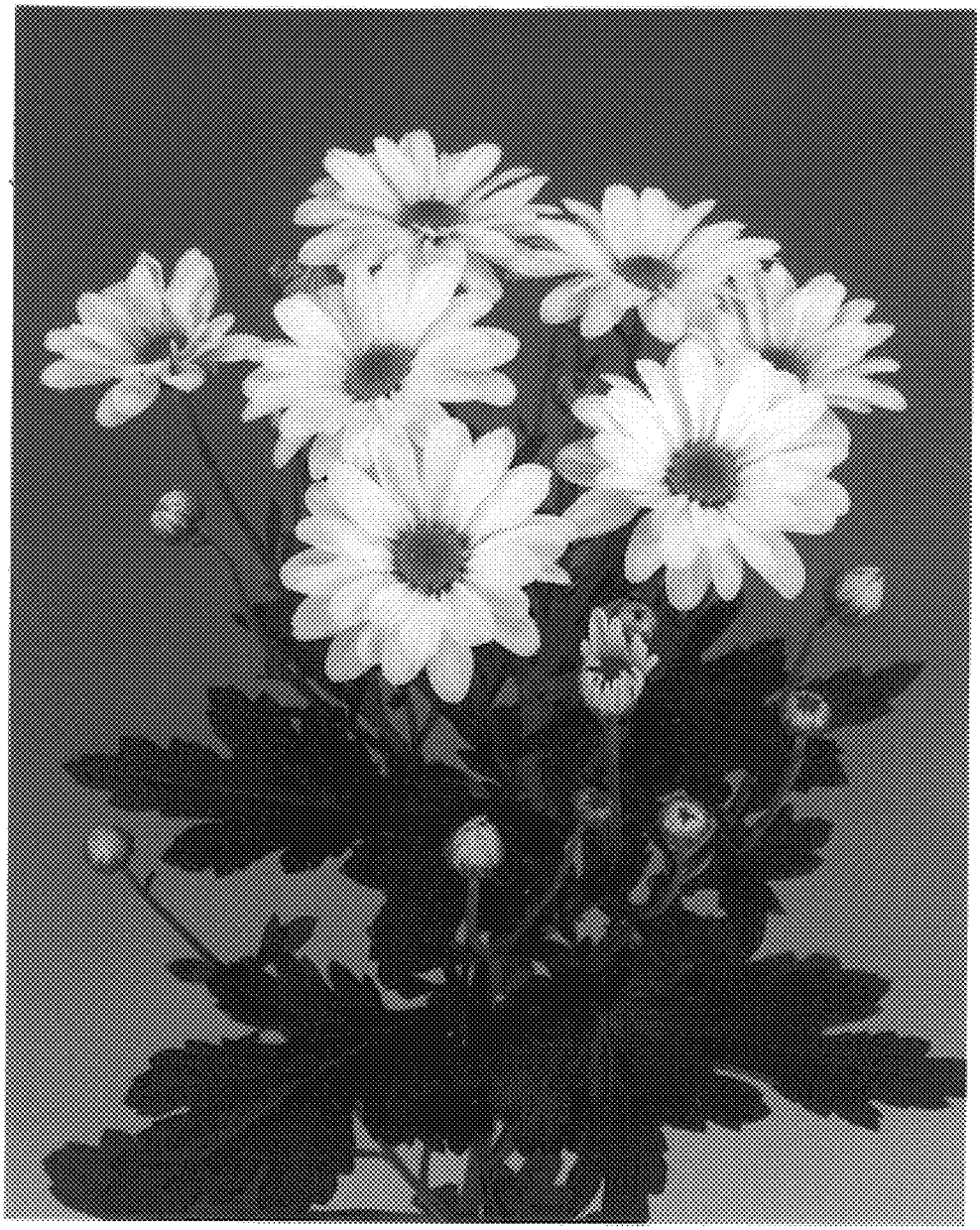
FIG. 1 shows a plant of the cultivar in full bloom.

This new variety of chrysanthemum is of the botanical classification Chrysanthemum morifolium. The observations and measurements were gathered from plants grown in April/May in a greenhouse in Rijsenhout, Holland in a photo-periodic controlled crop under conditions generally used in commercial practice. The greenhouse temperatures during this crop were at day-time between 18° C. and 25° C. and at night 20° C. After a long day period of 14 days, the photo-periodic response time in this crop was 50 days. After the long day period to flowering, growth retardants were applied 2 to 3 times in an average dose of 2.5 gram/liter water. No tests were done on disease or insect resistance or susceptibility. No tests were done on cold or drought resistance. This new variety produces medium sized blooms with white ray-florets and yellow-green disc-florets blooming on the plant for 5 weeks. This new variety of chrysanthemum has been found to retain its distinctive characteristics throughout successive propagations; however, the phenotype may vary significantly with variations in environment such as light intensity and temperature. To show the phenotype as described, 'White Reagan Mundo' can be planted without assimilation lightning (high pressure sodium lamps) between week 50 and week 40 of the next year under greenhouse conditions in Holland. With assimilation light (minimum level 2500 lux), it can be planted year round under greenhouse conditions in Holland.

The variety 'White Reagan Mundo' is a natural mutant of 'Pearl Reagan Mundo'. The variety 'Pearl Reagan Mundo' is a natural mutant of 'Reagan'. When 'White Reagan Mundo', 'Pearl Reagan Mundo' and 'Reagan' are being compared the following differences and similarities are noticed:

(A) The difference between 'White Reagan Mundo' and 'Pearl Reagan Mundo' is the flower color for which characteristic 'White Reagan Mundo' has been selected out of 'Pearl Reagan Mundo'. 'White Reagan Mundo' has white ray-florets instead of pale pink ray-florets. All other characteristics of 'White Reagan Mundo' and 'Pearl Reagan Mundo' are the same.

(B) The differences between 'Pearl Reagan Mundo' and 'Reagan', two varieties to which 'White Reagan Mundo' is related, are (1) flower form (2) flower size (3) flower color (4) spray formation and flower count and (5) tolerance for a lower night temperature for which characteristics 'Pearl Reagan Mundo' has been selected out of 'Reagan'. (1) Flower form: The ray-florets of 'Pearl Reagan Mundo' are less broad and more pointed and they are more upright. The flower-disc is smaller, greener and more regular. (2) Flower size: The flower is a little smaller. (3) Flower color: The flower color is paler. (4) The spray formation: The spray formation is more flat, less pyramidal, mostly a little wider and the flower count is higher. (5) Temperature tolerance: 'Pearl Reagan Mundo' and all its color mutants can be grown at a lower night temperature. The required minimum temperature for 'Reagan' (under all circumstances) is 17° C. Under high light conditions 'Pearl Reagan Mundo' can be grow at 14° C. This has been tested and confirmed in poor heated crops under high conditions flowering in Febrauary 1997 and 1998 in Italy and Spain. All other characteristics of 'Pearl Reagan Mundo' and 'Reagan' are similar.

The following is a description of the plant and characteristics that distinguish 'White Reagan Mundo' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour Chart, 1995 edition.

Table 1. Botanical Description of Cultivar 'White. Reagan Mundo'

Bud:
- *Size.*—Medium, cross-section 1.0 cm height 0.7 cm.
- *Outside color.*—Yellow 4 D.
- *Involucral bracts.*—2 rows, length 7 mm, width 3 mm.
- *Involucral bracts.*—Not present among disc-florets.
- *Involucral bracts.*—Yellow-green 146 B color.

Bloom:
- *Type.*—Single.
- *Height.*—Flat, 1.5 cm.
- *Size.*—Medium.
- *Fully expanded.*—6–6.5 cm.
- *Number of blooms per stem.*—Average of 12.
- *Performance on the plant.*—5 weeks.

Cultivar 'White Reagan Mundo':
- *Seeds* (*if crossed*).—Produced in small quantities, oval shaped Grey-brown 199 A, 2 mm in length.
- *Fragrance.*—Typical chrysanthemum, slightly.

Color:
- *Center of the flower* (*disc-florets*).—Immature yellow-green 144 A. Mature yellow-green 144 B.
- *Color of upper surface of the ray-florets.*—White 155 D.
- *Color of the lower surface of the ray-florets.*—White 155 D.
- *Tonality from distance.*—A spray mum with white flowers and a yellow-green disc.
- *Color of the upper surface of the ray-florets after aging of the plant .*—White 155 D.

Ray florets:
- *Texture.*—Upper and under side smooth.
- *Number.*—26–30 (two rows).
- *Cross-section.*—Convex.
- *Longitudinal axis of majority.*—Straight to slightly reflexing.
- *Length of corolla tube.*—Short, 0.4–0.6 cm.
- *Ray-floret margin.*—Entire.
- *Ray-floret length.*—2.8–3.3 cm.
- *Ray-floret width.*—0.7–0.9 cm.
- *Ratio length/width.*—Medium.
- *Shape of tip.*—Pointed.

Disc florets:
- *Disc diameter.*—Medium (1.3–1.5 cm).
- *Distribution of disc florets.*—Numerous, clearly visible at all stages of flowering.
- *Shape.*—Tubular.
- *Color.*—Yellow-green 144 A.
- *Receptacle shape.*—Conical raised.

Reproductive organs:
- *Stamen* (*present in disc florets only*).—Thick, 3 mm in length.
- *Number of stamen.*—4.
- *Stamen color.*—Yellow 12B.
- *Pollen.*—Present.
- *Pollen color.*—Yellow 12 B.
- *Styles* (*present in both ray and disc florets*).—Thin.
- *Style color.*—Yellow-green 144 A.
- *Style length.*—5 mm.
- *Stigmas.*—Yellow-green 144 A.
- *Stigma width.*—1 mm.
- *Ovaries.*—Enclosed in calyx.

Plant:
- *Form.*—A spray mum meant for erect culture.
- *Growth habit.*—Upright.
- *Growth rate.*—Moderate.
- *Height.*—100–115 cm.
- *Internodes.*—2.5–3.0 cm.
- *Spray formation.*—Corymbiform.
- *Stem color.*—Yellow-green 146 B.
- *Stem strength.*—Medium.
- *Stem brittleness.*—Absent.
- *Stem anthocyanin coloration.*—Present, a thin layer of Greyed-red 181 A.
- *Peduncle length.*—Near the top 11 cm, near the middle 18 cm, near the bottom 23 cm.
- *Peduncle color.*—Yellow-green 146 B.
- *Flowering response* (*photo-periodic controlled crop, not natural season*).—50 Days.

Foliage:
- *Color mature.*—Upper side green 137 A. Under side green 137 C.
- *Color immature.*—Upper side green 137 A. Under side green 137 C.
- *Size.*—Medium; length 12 cm, width 9 cm.
- *Quantity* (*number per single stem*).—26–32.
- *Shape.*—Lobed.
- *Texture upper side.*—Fleshy and glabrous.
- *Texture under side.*—Pubescent.
- *Venation arrangement.*—Palmate.
- *Shape of the margin.*—Crenated.
- *Shape of base of sinus between lateral lobes.*—Round.
- *Margin of sinus between lateral lobes.*—Converging sometimes asymmetric.
- *Shape of base.*—Rounded.
- *Apex.*—Mucronate.

TABLE 2

| | Differences with the comparison Varieties | | |
|---|---|---|---|
| | "WHITE REAGAN MUNDO" | "PEARL RGN MUNDO" | "REAGAN" |
| Color of the upper surface of the ray-florets | White 155 D | Red-purple 69 B but paler | Red-purple 75 B |
| Center of the flower | Yellow-green 144 B | Yellow-green 144 B | Yellow-green 151 C |
| Size of the flower | 6–6.5 cm | 6–6.5 cm | 6.5–7.0 cm |
| Number of blooms | Average 12 | Average 12 | Average 10 |

TABLE 2-continued

| | Differences with the comparison Varieties | | |
|---|---|---|---|
| | "WHITE REAGAN MUNDO" | "PEARL RGN MUNDO" | "REAGAN" |
| Temperature tolerance | 14° C. | 14° C. | 17° C. |

I claim:

1. A new and distinct variety of chrysanthemum plant as described and illustrated.

* * * * *